United States Patent [19]

Slettenmark

[11] Patent Number: 5,578,002
[45] Date of Patent: Nov. 26, 1996

[54] METHOD AND DEVICE FOR INTERNAL CLEANING OF AN IMPLANTED INFUSION SYSTEM

[75] Inventor: Bruno Slettenmark, Jaerfaella, Sweden

[73] Assignee: Siemens-Elema AB, Solna, Sweden

[21] Appl. No.: 268,123

[22] Filed: Jul. 6, 1994

[30] Foreign Application Priority Data

Jul. 16, 1993 [SE] Sweden ................................ 9302434

[51] Int. Cl.⁶ .................................................. A61M 1/00
[52] U.S. Cl. ................................................................ 604/65
[58] Field of Search ................................... 604/891.1, 82, 604/83–88, 141, 49, 53, 30–34, 65–67, 118

[56] References Cited

U.S. PATENT DOCUMENTS

| | | |
|---|---|---|
| 4,496,343 | 1/1985 | Prosl et al. ................................ 604/86 |
| 4,573,994 | 3/1986 | Fischell et al. . |
| 4,955,861 | 9/1990 | Enegren et al. ........................... 604/93 |
| 5,203,771 | 4/1993 | Melker et al. ............................ 604/86 |
| 5,395,324 | 11/1995 | Hinrichs et al. .......................... 604/86 |
| 5,417,673 | 11/1995 | Gordon .................................... 604/86 |
| 5,476,460 | 12/1995 | Montoluo ................................. 604/93 |

*Primary Examiner*—Manuel Mendez
*Attorney, Agent, or Firm*—Hill, Steadman & Simpson

[57] ABSTRACT

In a method for internally cleaning an implanted infusion system, having an infusion pump connected on its outlet side to a catheter via a nonreturn valve and a flushing port downstream of the nonreturn valve and upstream of the catheter, a first flow of cleaning fluid is passed through the infusion pump and the nonreturn valve. A second flow of secondary fluid is supplied through the flushing port, and a third fluid flow is discharged through the flushing port. A device for such cleaning has a pump such as a syringe connected to the flushing port for supplying the second flow of secondary fluid, for diluting or otherwise modifying the cleaning fluid passing through the infusion pump and the nonreturn check valve, and for discharging the third flow.

8 Claims, 5 Drawing Sheets

METHOD AND DEVICE FOR INTERNAL CLEANING OF AN IMPLANTED INFUSION SYSTEM

BACKGROUND OF THE INVENTION

1. Field of the Invention

The present invention is directed to a method and a device for internally cleaning an implanted infusion system, of the type having an infusion pump connected on its outlet side to a catheter via a nonreturn valve, a flushing port also being provided downstream of the nonreturn valve and upstream of the catheter, with a flow of cleaning fluid being passed through the infusion pump and the nonreturn valve.

2. Description of the Prior Art

Implantable infusion systems or infusers deliver medication or drugs usually in liquid form, such as an insulin solution, to the patient. For example, such an infuser can include a drug reservoir, a micropump with a nonreturn valve (i.e., a one-way valve, which permits fluid to flow away from the micropump but which blocks a return flow) and a catheter. A problem in such known infusers is that medication can become deposited on the interior surfaces of the pump and the nonreturn valve. A reduced volume delivered per pump stroke, valve leakage etc. are some of the disruptions which then can occur. If such a disruption occurs, the deposits in the system can be dissolved and the pump performances restored. For example, the reservoir can be filled with some type of cleaning or washing liquid which dissolves the deposits in question and allows the liquid to pass through the pump by activating the pump function. Since the washing liquid can be aggressive, toxic or unapproved as a drug etc., it is important to prevent the liquid from being pumped out of the catheter and coming into contact with body tissues. Allowing dissolved drug deposits to enter the body is also inappropriate, since this can cause immune reactions. For example, denatured insulin in the abdominal cavity can give rise to the formation of antibodies, and the patient can ultimately develop resistance to insulin. Therefore, no flow of washing liquid out of the catheter is desirable during the washing operation. An influx of body fluid into the catheter is similarly not desirable. Body fluids contain proteins which can contribute to catheter blockage and contamination of the so-called flushing port preceding the catheter. The presence of body fluid in this part of the infuser can have an adverse effect on the drug and on the life of the infuser.

In insulin pumps, this problem has hitherto been ignored and the patient has been exposed to unacceptable risks by pumping corrosive fluids out into the abdominal cavity of the patient or the following procedure has been used:

A drain, consisting of a liquid-filled flexible tube, is connected via a cannula to the flushing port with its other end positioned at a level lower than the tip of the catheter. As a result of the siphon effect, any free fluid in the abdominal cavity then flows back through the catheter out into the drain. Pumped washing liquid, often pumped with intermittent pump strokes, will then be distributed between the catheter and the drain in a ratio determined by the transient flow resistances. In favorable conditions, the quantity of washing liquid exiting through the catheter will be returned to the drain because of the retrograde siphon flow of body fluid in the catheter. This known method, however, has several major weaknesses.

Usually there is very little free liquid in the abdominal cavity, and any liquid therein is highly viscous. Since the interior lumen of the catheter is very small, typically 0.3 mm in diameter, the generation of an appreciable retrograde flow is uncertain. Moreover, there is a risk that the tip of the catheter becomes pressed against body tissue in the abdominal cavity, thereby preventing any retrograde flow, under such circumstances, however, it still will allow forward flow because an increase in the catheter pressure momentarily lifts the catheter tip. Thus, under certain circumstances, a valve function can develop in the catheter orifice, and there could be an outflow of hazardous substance into the abdominal cavity, despite the drainage provided.

Thus, the prior art methods provide neither desired control of the procedure nor patient safety.

SUMMARY OF THE INVENTION

An object of the present invention is to make washing of the interior of infusion systems with aggressive fluids possible without risk to the patient or to the infusion system, in already implanted infusion systems and in future systems equipped with a flushing port.

The above object is achieved in accordance with the principles of the present invention in a method and apparatus wherein the outlet of an infusion pump in an implanted infusion system is connected to a nonreturn valve, and a flushing port is connected between the nonreturn valve and a catheter, and wherein a first flow of cleaning fluid is passed through the infusion pump and the nonreturn valve into the flushing port, a second flow of secondary fluid is introduced into the flushing port from a location exterior of the subject in whom the infusion system is implanted, and a third flow of cleaning fluid mixed with the secondary fluid is discharged from the flushing port to a location exterior of the subject.

Thus, the invention is applicable to infusion systems with a so-called flushing port downstream of the pump valve but upstream from the catheter. A check can be performed with a cannula and syringe through this flushing port to ensure that the catheter is open and if this is not the case, an applied pressure/flow will often re-open the catheter and restore the function.

DESCRIPTION OF THE PREFERRED EMBODIMENTS

Figure 1A:
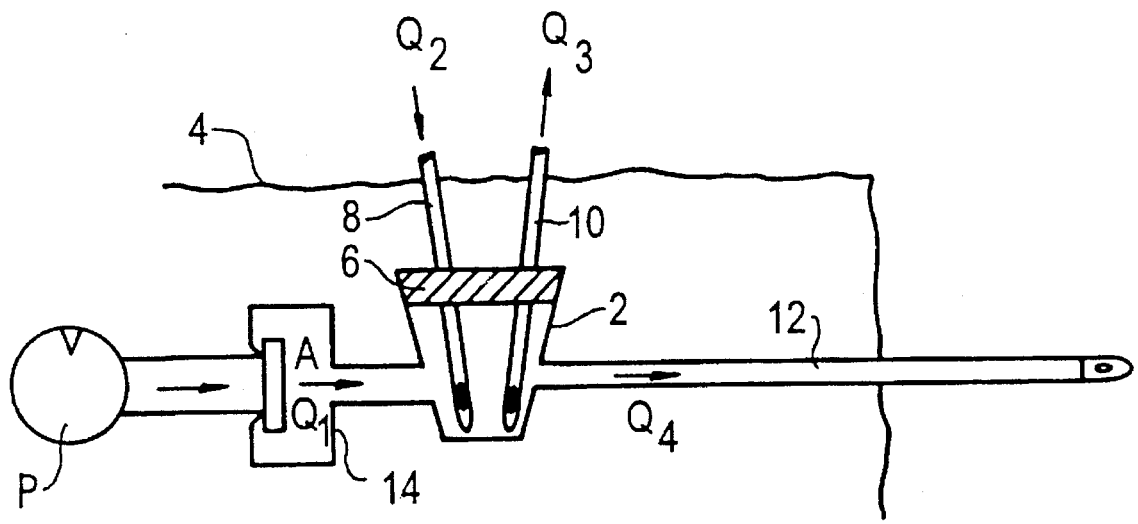
FIG. 1A is a schematic drawing of an implanted infuser illustrating the principles underlying the invention.

Cleaning or washing liquid is caused by a pump P to pass through a nonreturn valve 14 with a flow $Q_1$ and passes into the flushing port 2, as shown in FIG. 1A. The cleaning fluid is mixed in the flushing port 2 with another secondary liquid with a flow of $Q_2 \gg Q_1$, which is continuously injected with a cannula 8 inserted through the skin 4 and the flushing septum 6. The liquid mixture is extracted with a flow $Q_3$, through another cannula 10, inserted through the flushing septum 6, the flow $Q_3$ being in a very exact ratio to $Q_1$ and $Q_2$. In this way, the desired magnitude of the resultant outflow $Q_4$ of the liquid mixture through the catheter 12 can be controlled very exactly.

Generally the following applies:

$$Q_1+Q_2=Q_3+Q_4$$

and $$Q_2, Q_3 \gg Q_1$$

Usually, $Q_4=0$ is desired, whereby $Q_3=Q_2+Q_1$, but in certain instances either a very small but positive outflow ($Q_4>0$) is desirable, whereby $Q_1+Q_2>Q_3$, or a very small inflow ($Q_4<0$) is desirable, whereby $Q_3>Q_2+Q_1$. Thus, no liquid will enter the abdominal cavity ($Q_4=0$, or $Q_4<0$) or a very small, well-defined quantity of the strong washing liquid, which is diluted (typically 100-fold) to a harmless concentration or a chemically neutralized washing liquid ($Q_4>0$) enters the abdominal cavity.

The secondary liquid or fluid can be (a) neutral, e.g. distilled water, just to physically dilute the washing liquid or fluid to a harmless concentration, or (b) chemically active to neutralize the washing liquid or fluid for the purpose of making it harmless to body tissue. For example, the washing liquid or fluid can be a NaOH solution, and the secondary liquid or fluid can in case (a) be sterile water and in case (b) be a buffer solution which effectively reduces the pH value of the mixture, an acid solution etc.

Figure 1B:
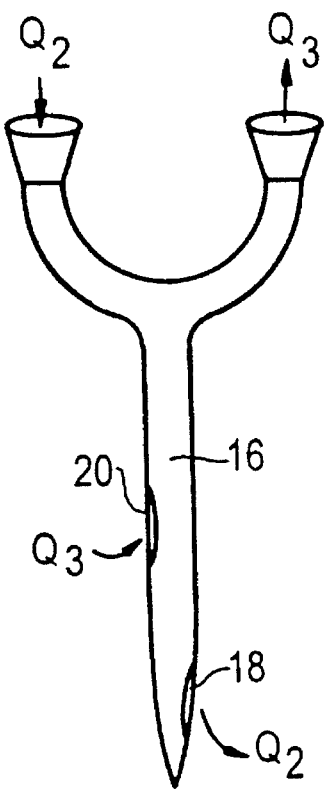
FIG. 1B shows a double-lumen cannula which can be used with the invention.

The two cannulae 8 and 10 for secondary and transport fluids can advantageously be replaced with a double-lumen cannula 16 (FIG. 1B) to facilitate the whole procedure and reduce the trauma to both the patient and the flushing septum (a small area is unable to withstand many punctures, is difficult to locate in a stout patient etc.). A relatively large distance between the orifices 18 and 20 for the respective flows $Q_2$ and $Q_3$ is desired to avoid any flow occurring straight from the orifice 18 to the orifice 20.

The device according to the invention makes it possible to retain, with great accuracy, a given ratio between the flows $Q_1$, $Q_2$ and $Q_3$ with simple equipment.

Figure 2A:
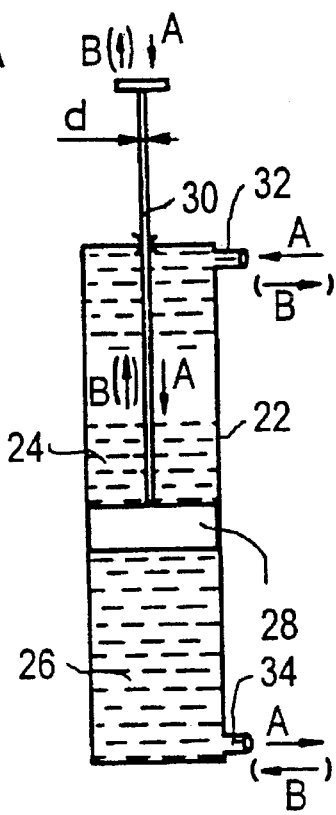
FIGS. 2A, 2B and 3 respectively show different embodiments of pumping means in the device according to the invention.

FIG. 2A shows a first embodiment of the pump means in the device according to the invention in the form of a syringe with a cylinder 22 in which a piston 28 is displaceable. The piston 28 can be manipulated with a piston rod 30. Each end of the cylinder 30 is provided with openings 32 and 34 for the intake and discharge of fluid as the piston 28 is moved.

When the piston 28 is moved in direction A in FIG. 2A, after the syringe has been connected to the flushing port 2, fluid is pumped out through the opening 34 at the same time as fluid is drawn in through the opening 32. Then the outflow $Q_{out}$ must be greater than inflow $Q_{in}$ into the cylinder 22 and the difference in flow magnitudes is determined by the dimension of the piston rod 30.

When the piston is moved in direction B in FIG. 2A, there is an outflow $Q_{out}$ through the opening 32 and an inflow $Q_{in}$ through the opening 34. Here, $Q_{in}>Q_{out}$.

Figure 2B:
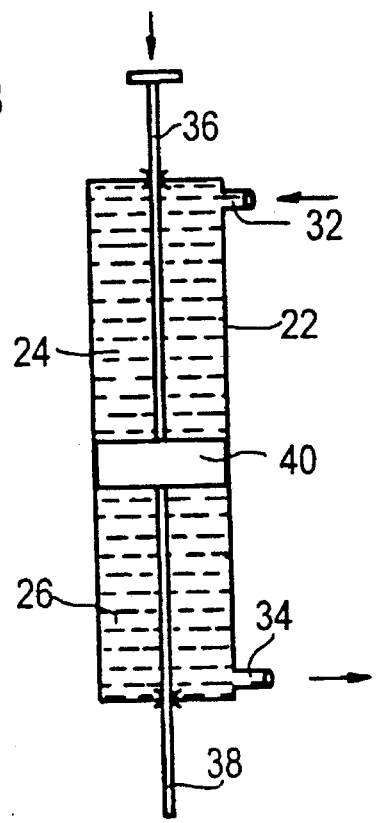

FIG. 2B shows an alternative version with piston rods 36 and 38 attached to either side of the piston 40. In this case, the flows $Q_{out}$ and $Q_{in}$, resulting when the piston 40 is moved, are equal.

Figure 3:
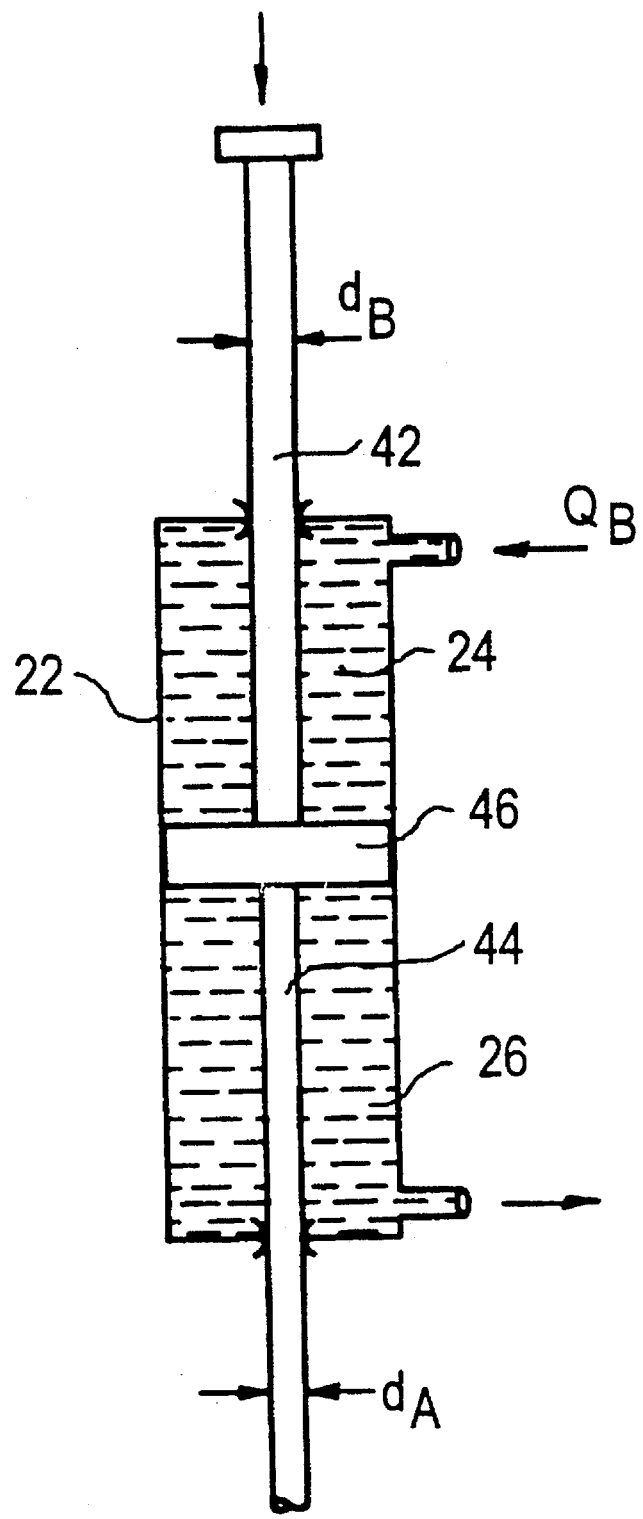

FIG. 3 shows another alternative version with two piston rods 42 and 44, the two piston rods 42 and 44 having different dimensions. If the diameter of the piston rod 42 is denoted by $d_B$ and the diameter of the piston rod 44 by $d_A$, the following conditions will apply to the flows $Q_A$ and $Q_B$ resulting when the piston 46 is moved downwardly in FIG. 3.

If $d_A<d_B$, then $Q_A>Q_B$,
If $d_A>d_B$, then $Q_A<Q_B$ and
If $d_A=d_B$, then $Q_A=Q_B$.

Thus, desired flows can be set by the appropriate choice of pistol rod dimensions. The condition $Q_3=Q_2+Q_1$, i.e. $Q_4=0$, thus can be realized through appropriate choice of $d_A$ and $d_B$, whereby $Q_B$ corresponds to $Q_3$ and $Q_A$ to $Q_2$.

Figure 4:
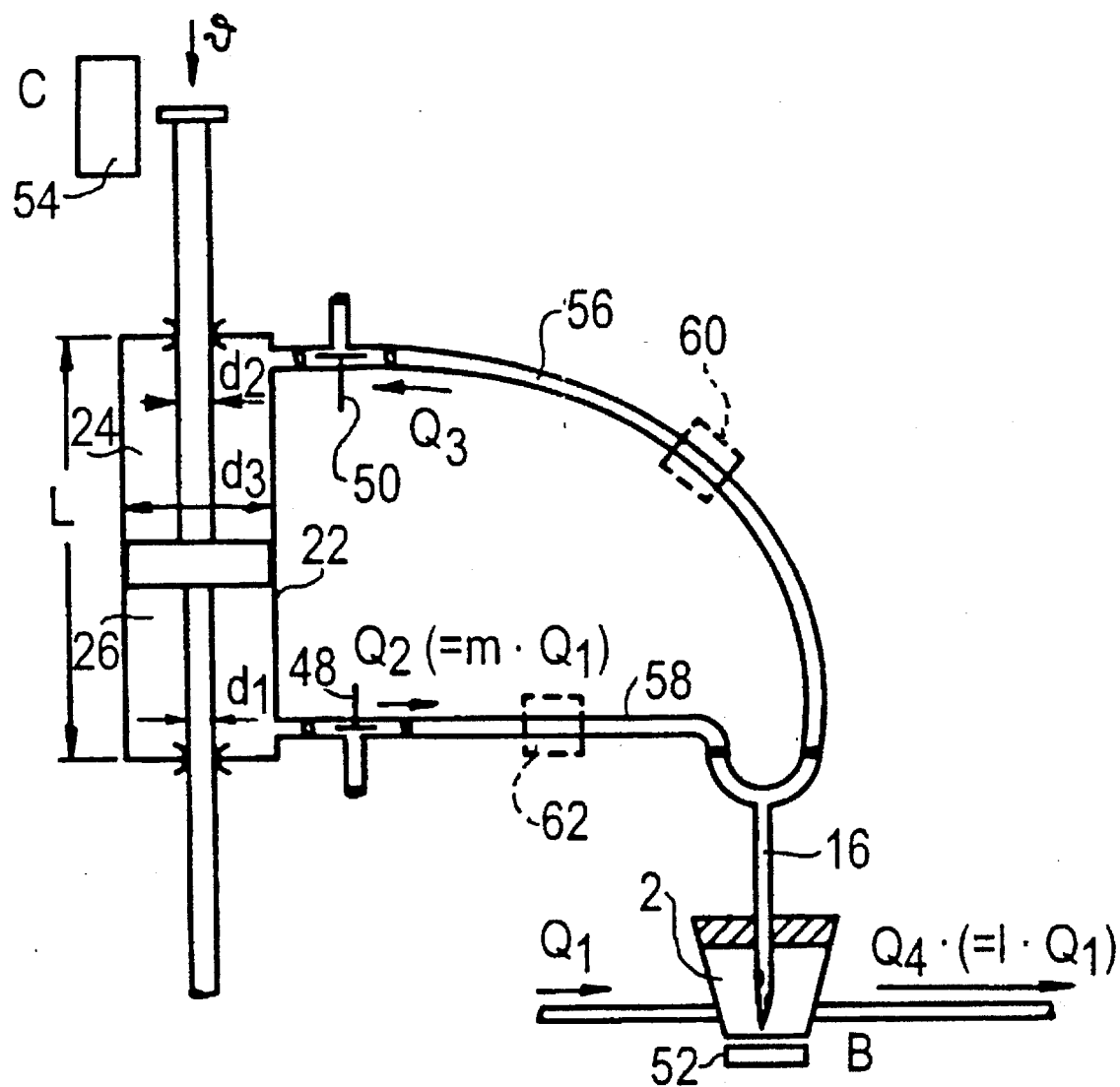
FIG. 4 illustrates the use of the double-lumen cannula in FIG. 1B and the pumping means in FIGS. 2B.

FIG. 4 shows the syringe in FIG. 2B connected by flexible tubes 56 and 58 and by a double-lumen catheter 16 to the flushing port 2.

At a given value for the flow $Q_1$, a dilution factor m and the flow $Q_4$ (cf. FIG. 4), the parameters $d_1$, $d_2$, $d_3$ and the feed velocity v can be selected and calculated respectively. One dimensioning example is as follows:

Dimensioning example

Assume that $Q_1, =10^{-10}$ m³/s (corresponding to the maximum flow of the pump of 1 μl/10 s, so-called bolus dose. There is one pump stroke per 10s, and each stroke gives 1 μl).

Duration=4,000 s, resulting in a total quantity of 0.4 ml.

Further assume that the dilution factor m=100, i.e.

$$Q_2=m \cdot Q_1.$$

Also assume that $Q_4=l \cdot Q_1$, where l is an optional factor, positive, negative or =0. Calculations give the following relationship:

$$d_1 = \left[ \frac{\frac{1-l}{m} \cdot d_3^2 + d_2^2}{1 + \frac{1-l}{m}} \right]^{1/2}$$

$$v = \frac{4Q_1}{\pi} \cdot \left[ \frac{1+m-l}{d_3^2 - d_2^2} \right]$$

If we now select
l=0 (i.e. $Q_4=0$)
$d_3=3 \cdot 10^{-2}$ m
$d_2=6 \cdot 10^{-3}$ m
we get
$d_1=6.68 \cdot 10^{-3}$ m
$v=14.9 \cdot 10^{-6}$ m/s
The length of the syringe is $L \geq 7 \cdot 10^{-2}$ m (stroke length $6 \geq 10^{-2}$ m).

To attain the intended accuracy, it is essential for both chambers of the syringe 24 and 26 to be filled, free from air, at the start of the procedure. Otherwise, the fluid medium will not be incompressible and the $Q_2/Q_3$ ratio will not remain reliably constant. In order to facilitate air-free filling, the syringe can be equipped with, e.g., three-way cock 48 and 50 according to FIG. 4, or some similar means through which the system can be degassed.

The following two examples describe how to effectively clean a catheter in accordance with the inventive method and device.

The infusion pump is delivering the flow $Q_1$, which is comprised of first 0.4 ml buffer solution followed by 0.4 ml of 50 mM NaOH and finally 0.6 ml buffer solution, i.e., a total volume of liquid of 1.4 ml. This liquid is continuously mixed with the secondary fluid supplied into the flushing port by a syringe and sucked out again such that the flow out through the catheter is zero or approximately zero, that is $Q_2 \approx Q_3$ or $Q_A \approx Q_B$ in FIGS. 2–4. The secondary fluid can have a purely diluting effect, but is preferably buffering, which gives a better result. For several reasons it is desirable to rinse with the secondary fluid during the whole procedure and not only in the phase during which NaOH is supplied. With a dilution factor m=100 the volume of the syringe will be 140 ml which is an impractically large syringe. In practice it has been found, however, that a dilution factor m=28, which corresponds to a syringe volume of 39 ml, gives excellent results in a device with $d_A=d_B$.

The flow rate through the infusion pump is, however, extremely low, about 0.1 µl/s, and the flow of secondary fluid is rather low too for a dilution factor m=28 or even m=100. Thus, there will be a very small flow in the flushing port and the agitating effect will be moderate. In a worst case, which may be caused by unfortunate positioning and/or design of the double lumen cannula used for the flushing, and with a small fluid volume flowing out through the catheter, that is in the case $d_A=d_B$, there could theoretically be no mixing or the mixing could be inadequate, such that the flows in the flushing port would be essentially laminar and too high a concentration of NaOH could be discharged through the catheter.

To avoid this risk and enhance the mixing effect in the flushing port, with the use of a syringe of reasonable size and in the case with $d_A=d_B$ the following procedure can be used.

The piston of the secondary fluid syringe is moved with an essentially constant velocity $v_1$, first in the forward direction with this velocity for a time $t_1$, then the piston is moved with the same velocity in the opposite direction for a time $t_2$ which is shorter than the time $t_1$. Thereafter the piston is moved in the forward direction for another period $t_1$ followed by movement in the opposite direction during a time $t_2$, and so on.

The time period $t_1$, can have a length from a few seconds to several minutes and the velocity of the piston $v_1$, is relatively high, so as to get a flow in the flushing port which is, e.g., 1000 times the flow from the infusion pump, that is m=1000, or even higher.

The flow of the pump is 0.1 µl/s as mentioned above and for a secondary flow of 100 µl/sec (m=1000) an effective mixing will be obtained in the flushing port for the geometric dimensions in question.

The average velocity $\bar{v}$ is given by $$\bar{v} = \frac{v_1 \cdot t_1 - v_1 \cdot t_2}{t_1 + t_2} = v_1 \cdot \frac{t_1 - t_2}{t_1 + t_2}$$

and is adapted such that the piston of the syringe will reach its end position at the same time or after the termination of the primary flow $Q_1$.

Another method of operating the device shown in, e.g., FIG. 2B is to move the piston of the secondary fluid syringe from one end position to the other and then back to the first end position, and so on. The piston is moved with the velocity which corresponds to the desired dilution, e.g. m=1000.

Both in this mode of operation and in the previously described one, the concentration of primary fluid will increase during the operation, since the secondary fluid is re-used for dilution of the primary fluid for a number of times. Independently of the velocity of the piston, and consequently independently of the value of the parameter m, the concentration of NaOH at the end of the procedure will be ≦0.4 ml 50 mM NaOH in 39 ml fluid volume in the secondary fluid syringe, that is the concentration will be 0.4/39=0.0103 ml caustic solution/ml fluid.

In the case with $d_A=d_B$ a total fluid volume of 1.2 ml will pass through the catheter out into the abdominal cavity. The concentration c in this fluid will be $$c \leq \frac{\left[ m \cdot \frac{0.4}{39} + 1 \right]}{m+1} \text{ ml caustic solution/ml fluid}$$

and for m=1000 c=0.0112 ml caustic solution/ml fluid which corresponds to a dilution of one part caustic solution per 88 parts secondary fluid. This dilution fulfills by a very wide margin the requirement for a harmless pH value of the fluid reaching the abdominal cavity, provided that a secondary fluid is used such as, e.g., the "dilution buffer" made by the company Hoechst.

Thus, with the above described examples of mode of operation safe mixing is obtained in the flushing port for every operating condition with a reasonable size of the secondary fluid syringe suitable for commercially available syringe pumps, and it is completely secured that the small volume of fluid which is passing out into the abdominal cavity is harmless.

Since the consequences could be grave if the device failed to work as intended, the system can be supplemented with those control functions which are deemed necessary to assure reliable function. Some examples are:

A. A device 52 which monitors the tip of the cannula to determine whether it is in the correct position inside the flushing port throughout the entire procedure.

B. A position sensor/speedometer 54 which checks that the piston rod is moving in the intended manner.

C. A flow sensor, especially for the return flow $Q_3$ but eventually also for the inflow $Q_2$. If there is no return flow $Q_3$ for some reason, e.g. because the cannula orifice is blocked or the like, the flow $Q_1+Q_2$ will pass out into the catheter. This is not necessarily dangerous but is inappropriate in any event. The flow sensor 60 in FIG. 4 ensures that $Q_3$ is close to the desired value. The sensor 60 can lie in the fluid path and does not have to be sterile, since the return flow does not have to be sterile. The sensor 60 can be a commercial mass flow meter or the like. (If the flow $Q_3$ is interrupted, the pressure in the interior of the syringe will drop to the vapor pressure of the fluid at the prevailing temperature, whereupon vapor bubbles will form, and the piston movement will continue, although against a higher resistance.)

If the flow $Q_2$ stops or is delivered to the wrong place, body fluid will be drawn back through the catheter (i.e. $Q_4=Q_3$) and be intermixed and transport $Q_1$, out in the return flow. Cleaning fluid will not enter the abdominal cavity of the patient. If there is no body fluid to extract, the sensor 60 will detect a small flow and issue an alarm signal. An inflow gauge 62 may still be desired/necessary (drawing of body fluid into the catheter/flushing port is undesirable). The gauge 62 must be sterile if it is to lie in the flow of fluid. The flow $Q_2$ can be measured outside the fluid pathway, e.g. with an autocorrelation meter, an ultrasonic Doppler meter, a laser Doppler meter, meters based on measurement of the Hall effect (electrically conductive fluid), etc. A non-homogenous fluid, to which, e.g. very small particles are added, might possibly be needed for a Doppler meter in order to give a signal diffused back with sufficient strength.

The equipment can advantageously be made of sterilized disposable articles of rubber and plastic, such as commercially available syringes. Piston operation can be accomplished with commercially available infusion equipment with appropriate performances. One major advantage with the equipment is that the same piston and piston rod provide both outflow and inflow. The momentary $Q_2/Q_3$ ratio is independent of fluctuations in the velocity v. In addition, a slow spatial variation in the diameter $d_3$ along the length of the syringe 22 only slightly affects the $Q_2/Q_3$ ratio, or not at all.

Figure 5A:
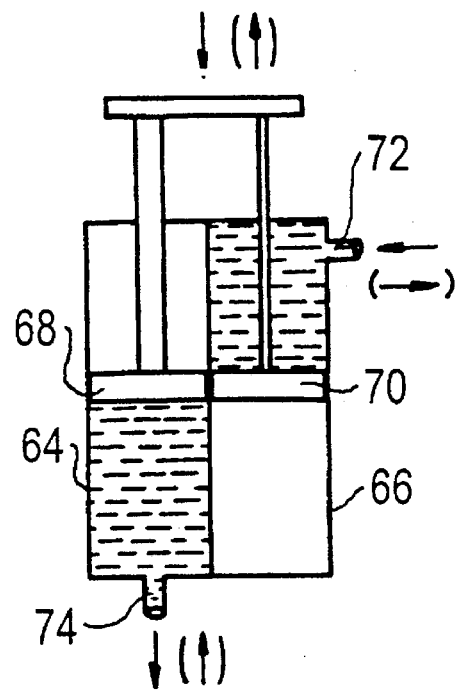
FIGS. 5A and 5B respectively show two alternative versions of the pumping means in the device according to the invention.
Figure 5B:
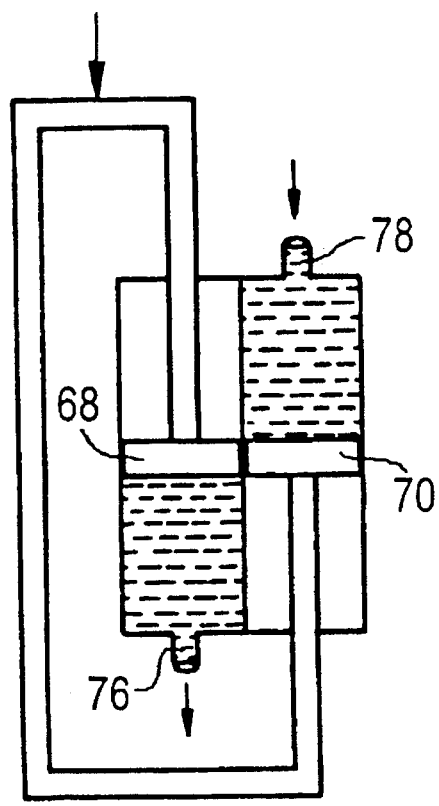

FIGS. 5A and 5B show two possible versions which, however, do not exhibit said advantages.

In FIG. 5 is thus shown one version of pumping means with two parallel cylinders 64 and 66, each with a piston 68 and 70, the pistons 68 and 70 being interconnected for joint movement. The cylinders 64 and 66 are devised with openings 72 and 74, and 76 and 78 respectively at opposite ends, whereby a flow of fluid is pumped out through one of the openings, and a flow of fluid is drawn in through the other opening, or vice-versa depending on the direction of movement of the pistons 68 and 70.

The flow $Q_1$ of cleaning fluid is very small (about $10^{-10}$ m$^3$/s), whereas the flows $Q_2$ and $Q_3$ can be, e.g., 100 times larger. A temporary (or constant) imbalance of, e.g., 5% between the flows $Q_2$ and $Q_3$ will then result in a large, undesirable inflow/outflow $Q_4=5 \cdot Q_1$. Such an imbalance can occur in the devices in FIG. 5 if extraordinary measures are not taken, but not in the device in FIG. 4. Even if relatively simple equipment is used with moderately low tolerance requirements and even if the piston is made of rubber, and is thus capable of deformation and possibly jerky movement, the piston is incompressible and does not change the $Q_2/Q_3$ ratio. The accuracy of the desired flow $Q_4$ is just as good or better than the accuracy attainable with very expensive and complex equipment, which would not be able to utilize sterilized disposable articles.

The invention has been described above as applied to a system with the catheter opening into the abdominal cavity, however, the invention is clearly applicable to systems with the catheter opening into other sites in the body, e.g. into blood vessels.

The above-mentioned secondary fluid or liquid can be a diluent fluid for purely physical dilution of the cleaning fluid. Such dilution is, however, often inadequate in rendering the diluted fluid harmless to body tissue, and therefore the secondary fluid often consists of a buffer solution. In theory, an acid could also be used as the secondary fluid.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for internally cleaning an implanted infusion system having an infusion pump with an outlet connected to a catheter via a nonreturn valve and with a flushing port disposed downstream of the nonreturn valve and upstream of the catheter, comprising the steps of:

generating a first flow of cleaning fluid through said infusion pump and said nonreturn valve and into said flushing port;

injecting a second flow of a secondary fluid into said flushing port from an extracorporeal location;

discharging a third flow of mixed secondary fluid and cleaning fluid from said flushing port to an extracorporeal location; and maintaining said third flow substantially equal to a sum of said first flow and said second flow.

2. A method as claimed in claim 1 comprising the additional step of:

maintaining said second and third flows substantially larger than said first flow.

3. A method as claimed in claim 1 comprising the additional step of maintaining said second and third flows substantially equal.

4. A method as claimed in claim 1 wherein the step of maintaining said third flow substantially equal to a sum of said first flow and said second flow comprises maintaining said third flow strictly equal to said sum of said first flow and said second flow.

5. A method as claimed in claim 1 wherein the step of generating a second flow of a secondary fluid comprises generating a second flow of a neutral fluid into said flushing port and thereby diluting said cleaning fluid in said flushing port.

6. A method as claimed in claim 1 wherein the step of generating a second flow of a secondary fluid comprises generating a second flow of a chemically active fluid in said flushing port for chemically modifying said cleaning fluid in said flushing port.

7. A method as claimed in claim 6 wherein the step of generating a second flow of a chemically active fluid into said flushing port for neutralizing said cleaning fluid in said flushing port.

8. A method as claimed in claim 1 comprising the additional step of reversing the respective directions of said second and third flows at least twice during a cleaning procedure.

* * * * *